(12) United States Patent
Saraswat et al.

(10) Patent No.: US 9,612,196 B2
(45) Date of Patent: Apr. 4, 2017

(54) IN-SITU OPTICAL DENSITY SENSOR

(71) Applicant: MASSEY UNIVERSITY, Auckland (NZ)

(72) Inventors: Mack Saraswat, Auckland (NZ); John Andrew Harrison, Auckland (NZ); Ralph Stefan Grand, Auckland (NZ); Frazer Kingsley Noble, Auckland (NZ); Lutz Robert Gehlen, Auckland (NZ); Matthew Alan Woods, Auckland (NZ); Sam Bartho, Auckland (NZ)

(73) Assignee: MASSEY UNIVERSITY, Auckland (NZ)

( * ) Notice: Subject to any disclaimer, the term of this patent is extended or adjusted under 35 U.S.C. 154(b) by 0 days.

(21) Appl. No.: 15/026,866

(22) PCT Filed: Oct. 3, 2014

(86) PCT No.: PCT/NZ2014/000213
§ 371 (c)(1),
(2) Date: Apr. 1, 2016

(87) PCT Pub. No.: WO2015/050464
PCT Pub. Date: Apr. 9, 2015

(65) Prior Publication Data
US 2016/0231242 A1 Aug. 11, 2016

(30) Foreign Application Priority Data
Oct. 4, 2013 (NZ) .................................. 616313

(51) Int. Cl.
G01N 21/00 (2006.01)
G01N 21/51 (2006.01)
G01N 21/59 (2006.01)

(52) U.S. Cl.
CPC ......... G01N 21/51 (2013.01); G01N 21/5907 (2013.01); *G01N 2201/0212* (2013.01); *G01N 2201/0227* (2013.01)

(58) Field of Classification Search
CPC .. G01N 21/253; G01N 21/0303; G01N 21/05; G01N 21/03; G01N 30/74
USPC ....................................................... 356/440
See application file for complete search history.

(56) References Cited

U.S. PATENT DOCUMENTS

| | | |
|---|---|---|
| 5,243,409 A | 9/1993 | Sagner |
| 6,958,693 B2 | 10/2005 | Rothgeb et al. |
| 7,410,269 B2 * | 8/2008 | Harrity ............. H05B 37/0272 362/101 |
| 8,730,477 B2 * | 5/2014 | Ruhland ............... G01S 7/4813 356/4.01 |
| 2005/0172721 A1 * | 8/2005 | Daigle .................. E21B 47/011 73/705 |
| 2005/0264817 A1 | 12/2005 | Havard et al. |

(Continued)

OTHER PUBLICATIONS

International Search Report and Written Opinion issued Mar. 18, 2015 in PCT/NZ2014/000213 (15 pages).

*Primary Examiner* — Tarifur Chowdhury
*Assistant Examiner* — Md M Rahman
(74) *Attorney, Agent, or Firm* — Debora Plehn-Dujowich

(57) ABSTRACT

The present invention relates to optical measurement devices and systems, and methods of using these systems and devices, and more particularly but not exclusively it relates to a system and apparatus adapted to measure optical properties in-situ.

19 Claims, 13 Drawing Sheets

Top-view

(56) References Cited

U.S. PATENT DOCUMENTS

2007/0291488 A1* 12/2007 Heathcock ......... H05B 37/0272
362/276
2013/0224851 A1 8/2013 Ljungmann et al.

* cited by examiner

Top-view

Cross-section view

Top-view

FRONT

SIDE

TOP

SECTION A-A

SECTION B-B

IN-SITU OPTICAL DENSITY SENSOR

CROSS REFERENCE TO RELATED APPLICATIONS

The present invention is filed under 35 U.S.C. § 371 as the U.S. national phase of International Application No. PCT/NZ2014/000213, filed Oct. 3, 2014, which designated the U.S. and claims the benefit of priority to New Zealand Patent Application No. 616313, filed Oct. 4, 2013, each of which is hereby incorporated in its entirety including all tables, figures and claims.

FIELD OF THE INVENTION

The present invention relates to optical measurement devices and more particularly but not exclusively it relates to a system and apparatus adapted to measure optical properties in-situ.

BACKGROUND TO THE INVENTION

Optical measurement devices are used in a variety of different applications. Optical measurement devices include devices that are used to measure or otherwise determine one or more properties of light such as intensity, colour, wavelength, or other characteristics. One type of optical measurement device is an optical density sensor. One type of optical density sensor is a cell density sensor which operates by shining light through a solution to a receiver. The optical density of the solution changes the amount of absorption or scattering of the passing light. The light receiver outputs a signal dependent on the intensity of the light received, which is in turn dependent on how much scattering or absorption the solution has caused.

Cell density sensors are used in biotechnology, chemical, brewing, wine making, fermentation, pharmaceutical, and other sectors of industry or research. For biotech applications, cell density sensors are ordinarily used to monitor growth of living cells in a cell culture.

A disadvantage with such optical measurement systems is that they typically require an onerous process in order to be used. The process includes repeated removal of a sample of the solution at consecutive time points under sterile conditions, applying that sample to a measurement device, recording the measurement and disposing of the sample. This process increases the risk of contamination, and the loss of sample volume from the solution.

It is an object of the present invention to provide an improved measurement system which overcomes or at least ameliorates some of the abovementioned disadvantage or which at least provides the public with a useful choice. Other objects of the invention may become apparent from the following description which is given by way of example only.

SUMMARY OF THE INVENTION

In one aspect the invention consists in a measurement device adapted for in situ light intensity sensing from within an environment comprising a housing adapted to enclose a control system and fluidly seal the control system from the environment, the housing having an outer wall and a channel fluidly connected to the environment at one or more locations, the control system comprising a controller, a light receiver component and a wireless data transmitter component, the light receiver disposed within the housing to receive light from the channel and output one or more signals indicative of light intensity, and wherein the control system is configured to receive the one or more signals indicative of light intensity from the light receiver, and output a signal indicative of light intensity to the wireless data transmitter.

In one embodiment, the control system further comprises a light source disposed within the housing to define a light path that extends from the light source, through the channel to the light receiver.

In one embodiment, a plurality of optical elements are disposed within the light path and are arranged to prevent light travelling substantially non parallel to the optical path.

In one embodiment, a plurality of optical elements are disposed within the channel and are arranged to prevent light incident to the channel.

In one embodiment, the channel extends between at least two locations on the outer wall of the housing to define a fluid flow path between the at least two locations.

In one embodiment, the channel defines a substantially straight path. In another embodiment, the channel defines a curved path, including for example, a channel having an 'S' shape.

In one embodiment, the channel meets the outer wall of the housing at an acute angle in at least one location.

In one embodiment, the channel is adapted to receive a spigot containing wireless power transfer electronics.

In one embodiment, the outer wall of the housing is substantially spherical or at least has a substantially circular profile. For example, the outer wall of the housing has a substantially spheroid profile, including oblate or prolate profiles.

In one embodiment, the outer wall of the housing is shaped to promote mobility when immersed in an environment where optical density is to be measured.

In one embodiment, the measurement device is not tethered, fixed or fastened to any one particular location within the environment.

In one embodiment, the control system further comprises a temperature sensor. In various embodiments, a temperature sensor is located so as to be in contact with the environment within which the device is present, for example, a liquid suspension. In one example, a temperature sensor is located proximate the outer wall of the housing and configured to provide temperature information to the controller. In one example, a temperature sensor is located proximate the light receiver and configured to provide temperature information to the controller. In a further example, a temperature sensor is located proximate the channel.

In one embodiment, the measurement device further comprises a propulsion mechanism operable to propel the device when in-situ, the controller further configured to output a signal to cause operation of the propulsion mechanism.

In one embodiment, the measurement device further comprises a buoyancy mechanism operable to cause floating or sinking of the device when in-situ, the controller further configured to output a signal to cause operation of the buoyancy mechanism.

In one embodiment, the controller is configured to output a signal to cause energisation of the light source.

In one embodiment, the wireless data transmitter is configured to transmit data to a wireless data receiving device.

In one embodiment, the control system further comprises a wireless power receiver, the receiver disposed within the housing proximate the channel so as to receive wireless power signals emitted from within the channel.

In one embodiment, the channel is adapted to receive a spigot containing one or more wireless power transfer components.

In one embodiment, the control system further comprises a plurality of gain setting resistors and the controller is configured to change the configuration of the resistors to affect one or more of the dynamic voltage range output from the light receiver and/or the intensity of the light source.

In one embodiment, the control system further comprises a wireless power receiver, the receiver disposed within the housing proximate the exterior surface so as to receive wireless power signals emitted proximate the exterior surface.

In one embodiment, the wireless power receiver is configured to provide a source of received charging power to a power source.

In one embodiment, the power source is configured to provide power to the control system including one or more components of the control system.

In one embodiment, the housing comprises a first and a second shell section, the first shell section having an engageable sealing surface adapted to couple with an engagable sealing surface of the second shell section, and form, when engaged, a substantially hermetic shell that encloses the control system.

In one example, the housing is a substantially hermetic homogeneous shell.

In one embodiment, the housing further comprises at a first aperture fluidly connected to the environment.

In one embodiment, a tube is disposed with the first aperture and the inside of the tube is arranged to fluidly connect with the environment and the outside of the tube is adapted to seal to housing from the environment.

In one embodiment, the housing further comprises two apertures and the tube is adapted to extend from the first aperture to the second aperture to define a fluid path through the housing.

In one embodiment, the tube is disposed within the light path.

In one embodiment, the tube is an optically transparent material.

In one embodiment, the tube is substantially cylindrical.

In one embodiment, the sealing surface of each of the first and second shell sections is threaded.

In one embodiment, the sealing surface of the first and second shell sections are adapted to engage by interference fit.

In one embodiment, the sealing surface of the first and second shell sections are adapted to compress about an o-ring or sealing device.

In one embodiment, the first and second shell sections are adapted to be chemically or thermally bonded together.

In another aspect the invention broadly consists in a measurement device adapted for in situ light intensity sensing from within an environment comprising a housing adapted to enclose a control system and fluidly seal the control system from the environment, the housing comprising:

a first and a second shell section, the first shell section having an engageable sealing surface adapted to couple with an engagable sealing surface of the second shell section, and form, when engaged, a substantially hermetic shell that encloses the control system.

In one embodiment, the housing further comprises at a first aperture fluidly connected to the environment.

In one embodiment, a tube is disposed with the first aperture, the tube adapted to fluidly connect the environment to the inside of the housing.

In one embodiment, the tube is an optically transparent material.

In one embodiment, the tube is substantially cylindrical.

In one embodiment, the housing has two apertures and the tube is adapted to extend from the first aperture to the second aperture to define a fluid path through the housing.

In one embodiment, the sealing surface of the first and second shell sections is threaded.

In one embodiment, the sealing surface of the first and second shell sections are adapted to engage by interference fit.

In one embodiment, the sealing surface of the first and second shell sections are adapted to compress about an o-ring.

In one embodiment, the shell is substantially spherical or at least has a substantially circular profile.

In one embodiment, the shell is shaped to promote mobility when immersed in the environment.

In one embodiment, the shell is not tethered, fixed or fastened to any one particular location within the environment.

In one embodiment, the first and second shell sections are adapted to be chemically or thermally bonded together.

In another aspect the invention broadly consists in a system comprising a sensor adapted to measure optical density from within an environment and a data processing device, the sensor comprising a housing adapted to enclose a control system and fluidly seal a control system from the environment, the housing having an outer wall and a channel fluidly connected to the environment at one or more locations, the control system comprising a controller, a light receiver component and a wireless data transmitter component, the light receiver disposed within the housing to receive light from the channel and output one or more signals indicative of light intensity, and wherein the control system is configured to receive the one or more signals indicative of light intensity from the light receiver, and output a signal indicative of light intensity to the wireless data transmitter, wherein the data processing device comprises a wireless data receiver configured to receive data transmitted by the wireless data transmitter.

In another aspect the invention broadly consists in a system comprising a sensor device adapted to measure optical density from within an environment and a data processing device, the sensor device comprising a wireless data transmitter configured to wirelessly transmit a signal indicative of an optical density measurement to the data processing device, and the data processing device comprising a receiver adapted to receive a signal indicative of optical density measurements.

In one embodiment, the data processing device is configured to store data received by the wireless data receiver on a storage device.

In one embodiment, the sensor device has an onboard data storage unit. For example, the sensor device has an on-board data storage unit to complement or substitute for the data processing device, for example as a support system in case of network malfunction and other power outages so as to retrieve data.

In one embodiment, the data processing device is configured to compute one or more statistical calculations on the stored data.

In one embodiment, the data processing device is configured to determine a measure of the optical density within the channel.

In one embodiment, the data processing device is configured to display a value indicative of the measure of the optical density within the channel to a display.

In one embodiment, the data processing device is configured to store data indicative of the time data is received from by the wireless data receiver.

In one embodiment, the data processing device is configured to interface with one or more other data processing devices.

In one embodiment, the data processing device comprises a wireless data transmitter adapted to transmit a signal indicative of a measurement to be taken, and the sensor further comprises a wireless data receiver adapted to receive the signal indicative of an optical density measurement to be taken.

In another aspect the invention broadly consists in a measurement system comprising an in situ light intensity sensor operable to measure optical density from within an environment and a data processing device, wherein the data processing device comprises a wireless data transmitter adapted to transmit a signal indicative of a measurement to be taken, and the sensor comprises a wireless data receiver adapted to receive the signal indicative of an optical density measurement to be taken and operate to take a measurement.

In one embodiment, the device is configured to perform one or more of the following steps: store data received by wireless data receiver on a storage device, compute one or more statistical calculations on the stored data, and determine a measure of the optical intensity within the channel, output a value indicative of the measure of the optical intensity within the channel to a display, store data indicative of the time data is received from by the wireless data receiver, transmit the stored data to one or more portable computation devices, or display received data.

In another aspect the invention broadly consists in a control system comprising a controller adapted for use in the measurement device and configured to output a signal to energise a light source in the measurement device, receive information indicative of an optical intensity measurement from a light receiving device, output information indicative of an optical intensity measurement to a wireless data transfer device.

In one embodiment, the controller is further configured to store information indicative of an optical intensity measurement received from a light receiving device.

In one embodiment, the measurement device comprises a power source and the control system is configured to measure the power from the power source.

In one embodiment, the control system further comprises a plurality of gain setting resistors and the controller is configured to change the configuration of the resistors to affect one or more of the dynamic voltage range output from the light receiving device and/or the light intensity of the light source.

In one embodiment, the controller is a microprocessor.

In one embodiment, the control system is further configured to output a signal operable to control or at least initiate operation of one or more of a propulsion mechanism or buoyancy mechanism.

In another aspect the invention broadly consists in a charging station comprising a base and a spigot and adapted to support a measurement device adapted for in-situ optical density sensing from within a fluid environment, wherein the base and/or the spigot are adapted to enclose one or more wireless power transfer components, and wherein the measurement device comprises a housing adapted to enclose one or more wireless power receiver components and the housing has a channel fluidly connected to the environment at one or more locations, and wherein the spigot is adapted to engage the channel to support the measurement device on the charging station.

In another aspect the invention broadly consists in a method of measuring optical density using a device, system, or housing according to any previous statement wherein the method comprises providing the device, system, or housing, operating the controller to receiving a signal from the light receiver and outputting a signal to the wireless data transmitter.

In another aspect the invention broadly consists in a method of charging the power source in the device according to any previous statement, wherein the method comprises providing the charging station, providing the measurement device, engaging the measurement device with the base and/or spigot of the charging device, and energising the one or more wireless power transfer components.

In other aspects, the invention relates to a device, system, housing or station as herein described or shown in any one or more of the accompanying figures.

Other aspects of the invention may become apparent from the following description which is given by way of example only and with reference to the accompanying drawings.

As used herein the term "and/or" means "and" or "or", or both.

As used herein "(s)" following a noun means the plural and/or singular forms of the noun.

The term "comprising" as used in this specification and claims means "consisting at least in part of". When interpreting statements in this specification and claims which include that term, the features, prefaced by that term in each statement, all need to be present, but other features can also be present. Related terms such as "comprise" and "comprised" are to be interpreted in the same manner.

As used herein, when the context allows the term "proximate" includes "at".

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7).

The entire disclosures of all applications, patents and publications, cited above and below, if any, are hereby incorporated by reference.

This invention may also be said broadly to consist in the parts, elements and features referred to or indicated in the specification of the application, individually or collectively, and any or all combinations of any two or more of said parts, elements or features, and where specific integers are mentioned herein which have known equivalents in the art to which this invention relates, such known equivalents are deemed to be incorporated herein as if individually set forth.

BRIEF DESCRIPTION OF THE DRAWINGS

The invention will now be described by way of example only and with reference to the drawings in which.

DETAILED DESCRIPTION OF THE INVENTION

Figure 1:
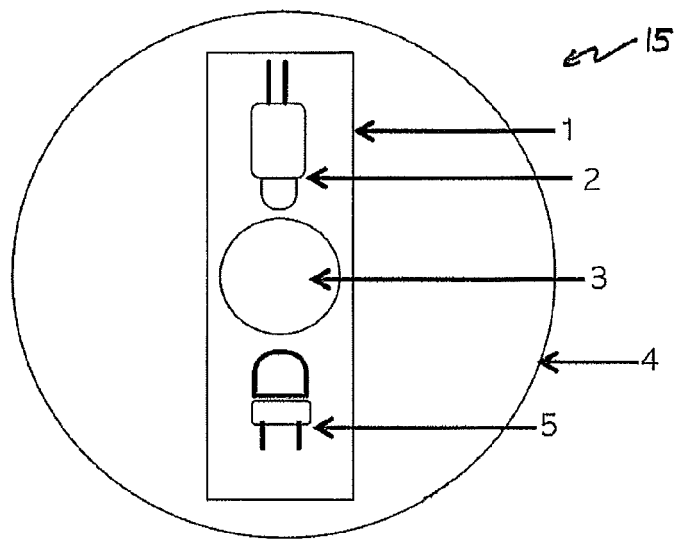
FIG. 1 shows an embodiment of the sensor in schematic form.

Growth in a living cell is an orderly increase in the amount of cellular components. In most living organisms, growth involves the increase in cell mass, duplication of the genetic material (DNA) followed by cell division. The division of cells increases cell number and hence the concentration of cells in a growth medium. A method of estimating cell concentration is by measuring turbidity of a suspension of cells in a liquid medium using photometry. Particle size objects, such as bacteria, suspended in a liquid scatter light that passes through the suspension. This scattering reduces the intensity of the light that is directly transmitted through the suspension. To a human eye, the suspension appears to be turbid or "cloudy". As more light is scattered with increasing cell concentration, the reduction in light intensity can be used to measure the concentration of cells.

Expressing cell growth mathematically, the intensity I of the light after it has passed through a solution or particle suspension is equal to the intensity $I_0$ of the incident light, multiplied by $10^{-N/N_{10}}$, where N is the concentration of particles in suspension and $N_{10}$ is the concentration of particles which gives a tenfold decrease in the light intensity.

$$I=I_0 \cdot 10^{-N/N_{10}} \text{(Beer-Lambert Law)}$$

On rearranging the equation and taking the logarithm to the base 10;

$$\log I/I_0 = \log 10^{-N/N_{10}} \text{ or } -\log I/I_0 = N/N_{10}$$

The term $-\log I/I_0$ is known as absorbance or optical density (OD) of a solution or suspension. Optical density is a function of the wavelength of the light and the optical path length through the suspension. Optical density or turbidity of a suspension of cells can—after calibration—be directly converted into cell concentration.

Existing probes have been designed and previously reported for large-scale fermentors or bioreactors. At the laboratory level, bacteria, yeast, fungi or mammalian cells are cultured in glass flasks and incubated at set temperatures in a shaker-incubator. Briefly, live or cryopreserved cells are inoculated into a growth medium, containing required growth supplements, inside a glass flask. This forms a broth of culture media and suspended particulates. The flasks are kept inside a temperature controlled shaking incubator to induce the cells to multiply. To monitor cell growth, aliquots of culture broth are taken manually from the flasks at regular time intervals, and measured using a spectrophotometer. The accurate monitoring of cell growth is—essential for many downstream applications and this offline measurement technique is cumbersome, time consuming, and prone to contamination and human error.

Embodiments of the invention relate to a sensor that is immersible in a solution the optical density of which is desired to be measured. Embodiments of the invention also relate to a system adapted for use with the sensor. The sensor is adapted to wirelessly communicate information to an information processing system and does not require manual removal of a sample or manual use of a spectrophotometer.

FIG. 1 shows a particular embodiment of the sensor 15 in schematic form. The sensor has a housing 4 which substantially encapsulates a plurality of components including a light source 2 and a light receiver 5 configured to receive light from the light source 2. The receiver 5 can directly face the light source, or the receiver 5 can be arranged such that emitted light is adequately guided by the optical properties of nearby or incident components. In some embodiments where luminance of the solution is desired to be measured, the light source is omitted.

The light source is configured to emit light when provided with an appropriate electrical stimulus. In one example, the light source is a light emitting diode (LED) or similar device which emits light when a voltage is applied. In certain embodiments the light receiver is a photodiode, phototransistor or similar device. The light receiver 5 is configured to output a signal indicative of the light intensity received. The light source 2 and receiver 5 are at least closely matched in terms of the wavelengths upon which they can efficiently transmit or receive. Further, the particular operation wavelength may be selected depending on the absorption properties of a solution desired to be tested. For example, the operation wavelength is aligned with or proximate to a peak absorption wavelength of a solution to be tested to optimise absorption efficiency and dynamic range of the measurements.

The light source 2 and light receiver 5 are located a specific distance apart such that an optical path is located therebetween. A channel 3 is located within the optical path such that light emitted from the light source 2 passes through the channel and to the receiver 5. The channel 3 has at least one opening fluidly connected with the exterior of the housing 4 such that the solution or suspension fills the channel when the sensor is immersed. The intensity of the light received by the light receiver 5 is indicative of the optical density of the substance within the optical path.

In some configurations the sensor has a number of collimating devices arranged within the channel 3 and optionally also the light path between the light source 2 and light receiver 5 to lower the acceptance angle of the light reaching the receiver and to reduce the amount of light scattered, or reflected off the sides of the channels into the light receiver. Preventing or mitigating the amount of ambient or scattered light from reaching the receiver improves measurement performance. The collimating devices comprise reflective, absorptive, or dispersive optical components having a geometry that provides scattering of the light incident upon it. FIGS. 8 to 11 illustrate configurations of the sensor with ridge like collimating devices 23 arranged within the channel 3 that have the effect of enabling a lower acceptance angle of light to the light receiver, and reducing the reflectance of the channel.

Figure 8:
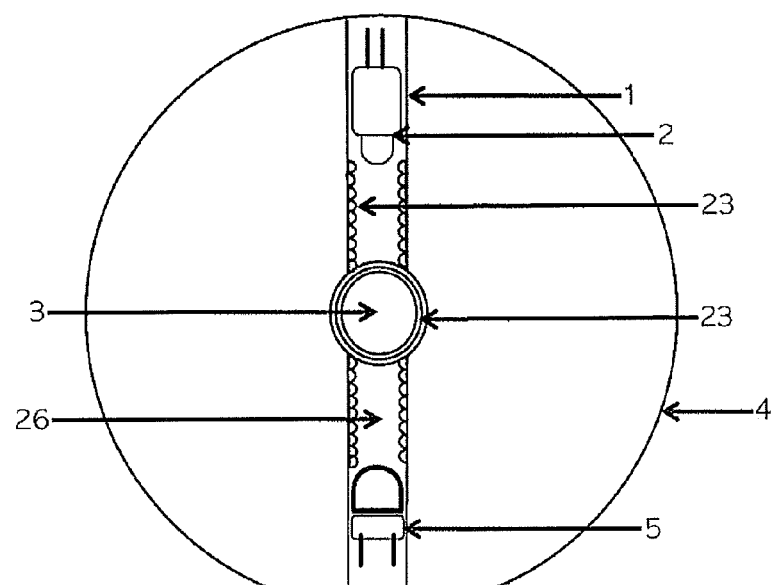
FIGS. 8 to 10 show light and fluid channels arranged within the sensor.
Figure 9:
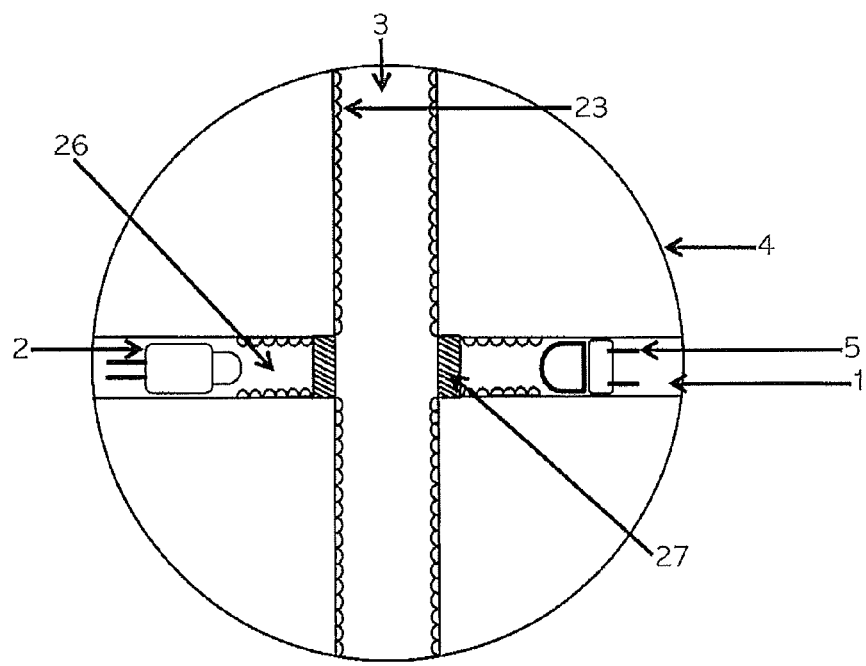
Figure 10:
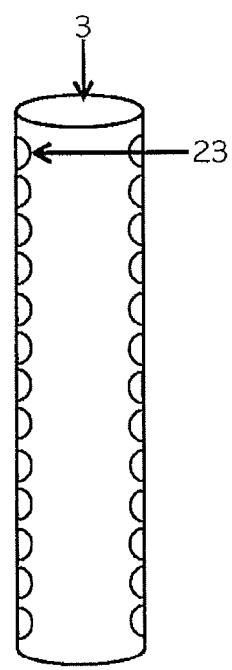

FIGS. 8 and 9 illustrate collimating devices 23 arranged within the light path 26 and transparent members 27 fluidly sealing the light source and light receiver portions of the light path from the channel 3. The collimating devices 23 are optimally arranged when only light travelling substantially parallel to the channel or light path enters the light receiver. Arrangement of the light path and channel in a substantially perpendicular geometry further improves measurement performance.

In some embodiments the housing has two openings such that the channel 3 extends from one side of the housing 4 to another to create a fluid flow path. This allows fluid to flow through the channel 3 as it is circulated by the natural stirring motion induced by a shaking incubator.

In some embodiments the channel is a cylinder which has a curved inner surface shape that advantageously reduces the chance of bubbles forming in the cavity and affecting the light path. In other embodiments, such as those where bubbles are not a concern, the channel is circular or square or polygonal in cross section. The use of glass or other hydrophilic material to form the channel decreases the tendency of bubbles to stick to the surface. In certain embodiments the channel is sealed to the sensor shell by mechanical seals such as o-rings, or it is chemically bonded by materials such as viscous sealant.

Figure 11:
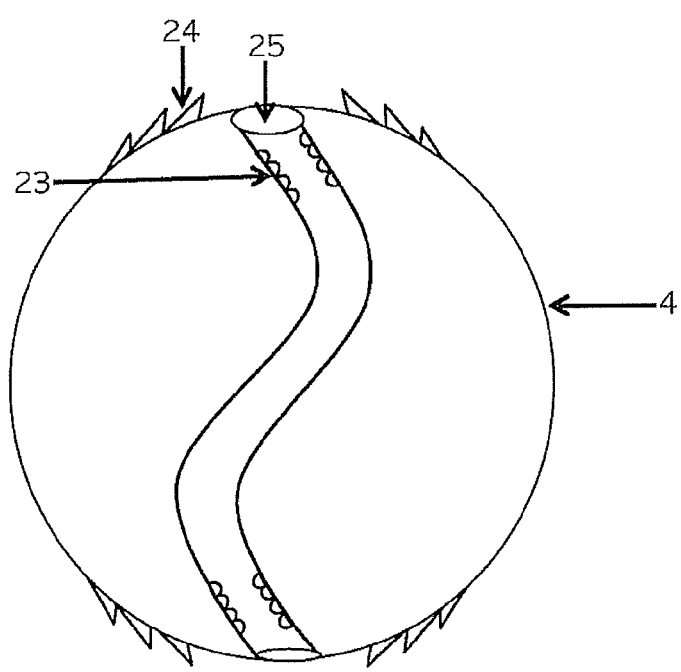
FIG. 11 shows an example of a sensor having an 'S' shaped fluid channel.

In some embodiments the channel 3 has entry ports 25 angled with respect to the sensor surface or a channel that is at least a serpentine shape. FIG. 11 shows an example of a sensor having an 'S' shaped channel 25 and angled entry ports. The 'S' shaped channel also helps to prevent ambient light from reaching the light receiver by blocking the line of sight trajectory of light entering the tunnel.

In some configurations a plurality of fins 24 are arranged on the sensor surface such that when immersed within a stirred solution the fins cause the sensor to spin. The fins in combination with the 'S' shaped channel promote pumping of the fluid through the channel. A shorter light path through the fluid enables use in higher OD solutions and/or the use of a lower power light source.

In one embodiment the sensor housing could be constructed using 3D printing techniques. A minimum wall thickness is used to ensure structural integrity is maintained during the sensor lifetime. Selective Laser Sintering 3D printing limitations for acrylic based photopolymer or nylon plastic: Objects must be manifold, minimum detail of 0.2 mm, minimum wall thickness of 0.7 mm, maximum temperature of 80° C.

In various embodiments the sensor housing is formed from multiple shell components, such as two hemispheres. The shell components are, for example, chemically or mechanically fastened together to encapsulate the internal components. Mechanical fastenings to secure each shell component include threaded or interference type connections. In some embodiments the shell components comprise two substantially hemispherical shell sections.

Each shell section has a mating surface where the shell sections are to oppose and engage. For example, the mating surface has a threaded connection complimentary to the opposing shell sections such that the shell sections can be screwed together. Alternatively, the mating surface of each shell section is sized to engage with an interference fit and therefore allow the use of non circular engaging surfaces. The housing is then completed by applying pressure to join the two shell sections and force the engagement of the mating surfaces. One or more sealing devices such as o-rings or semi viscous sealant may be employed to ensure leak proof engagement of the shell sections. In another embodiment, sealing is by friction, welding, or other engagement to ensure leak proof engagement, for example so as to form a homogeneous surface.

An optimum form of the sensor 15 for facilitating movement when immersed in a solution is that of a spherical form such as shown in the figures. However, in certain embodiments other forms that facilitate movement of the sensor, or at least do not substantially prevent movement, within a moving solution are utilised. For example, a substantially cylindrical or elliptically shaped housing form, a spheroidal form, or any other curved surface shaped housing form is utilised.

The outer surface of the sensor can include dimples or spikes. Impressions can help reduce fluid drag or provide traction to resist or reduce movement in fast moving fluids. Spikes can be provided where it is desired that the sensor embed itself in material on the bottom of the solution. For example, the sensor can be used in a stream of fluid where measurements are desired to be taken, such as a riverbed. The spikes help to fix the sensor in one location with respect to the stream.

To further facilitate movement of the sensor within an agitated solution, the outer surface of the sensor may include one or more fluid dynamic surfaces operable to impart kinetic energy to the sensor from the solution, or by an induced rotation of the shell with respect to the solution. The surfaces may comprise fins, contours, impressions or depressions joined to or formed in the outer sensor surface.

In some embodiments the sensor is constructed to have an eccentric weight distribution. This can assist in movement of the circulating fluid through the channel, or to preferentially align the channel with a particular direction, such as that of a flow path of a solution.

In some embodiments the light source 2 and receiver 5 are mounted to an electronics substrate 1 that is, in turn, releasably mounted to or within the housing 4. When mounted to the substrate 1, the light source and receiver may be readily removed from the sensor 15 and replaced with other combinations. This may allow the selection of particular operation wavelengths and light intensities depending on the solution desired to be tested. In some embodiments the substrate 1 is a circuit board able to flex such that it may easily fit within packaging constraints that sensor housing may impose. However, it is ideal that the light source 2 and receiver 5 are rigidly spaced apart such that alignment is maintained and movement or vibration has no substantial effect on the accuracy of the optical components. One or more guide lugs can be provided within the housing to facilitate repeatable and stable mounting of the substrate 1.

Figure 2:
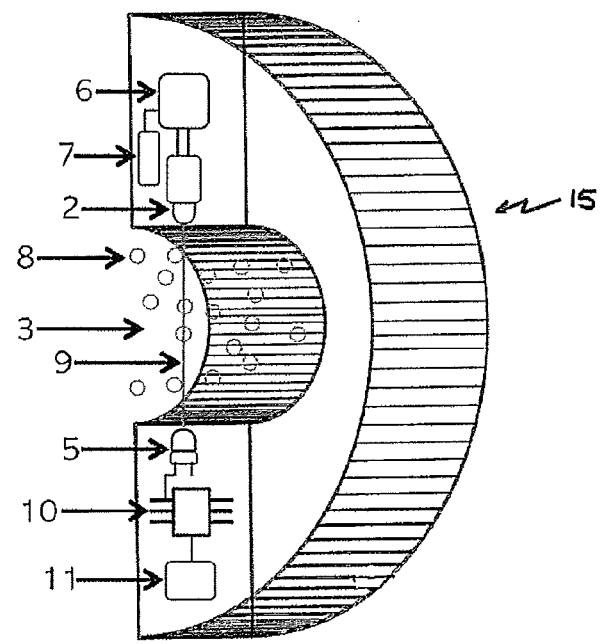
FIG. 2 shows a cross section of the sensor of FIG. 1.

FIG. 2 shows a cross section of the sensor of FIG. 1 showing the channel 3 disposed in the light path 9 between the light source 2 and the light receiver 5. The channel 3 is open to receiving solution 8 which causes absorption or scattering of light within the channel and light path.

FIG. 2 also shows a control unit or controller 10 that is configured to connect to the light source 2, the light receiver 5, a power source 6 and a wireless communications interface 11. The control unit is a microprocessor having at least one or more analogue-to-digital converter (ADC) inputs, one or more digital outputs and/or serial data transmission and receiver pins for communication with external protocol capable devices.

Figure 6A:
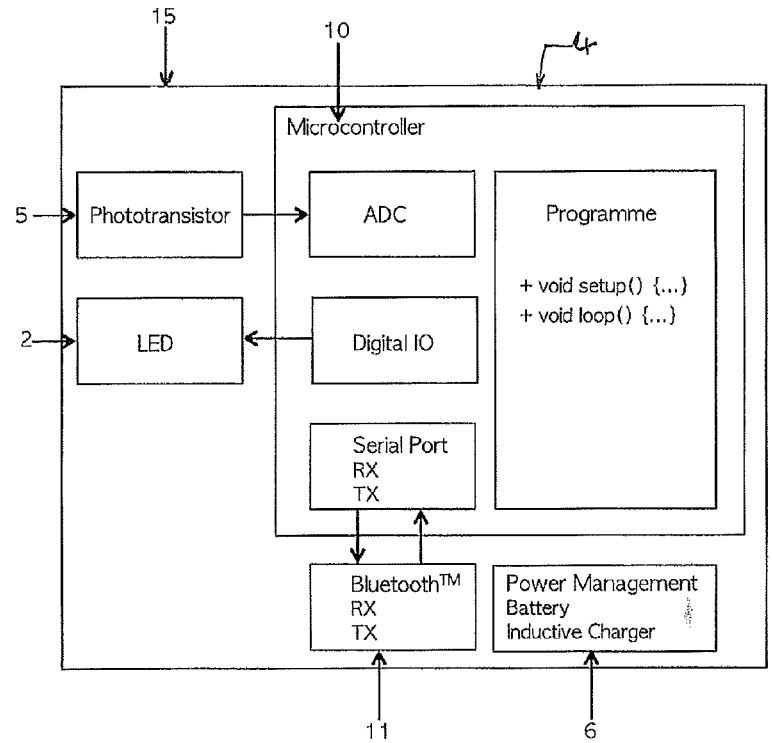
FIG. 6 shows a schematic of the components of FIG. 2 in further detail (FIG. 6A), and a schematic of the components of FIG. 2 with a temperature sensor (FIG. 6B).
Figure 6B:
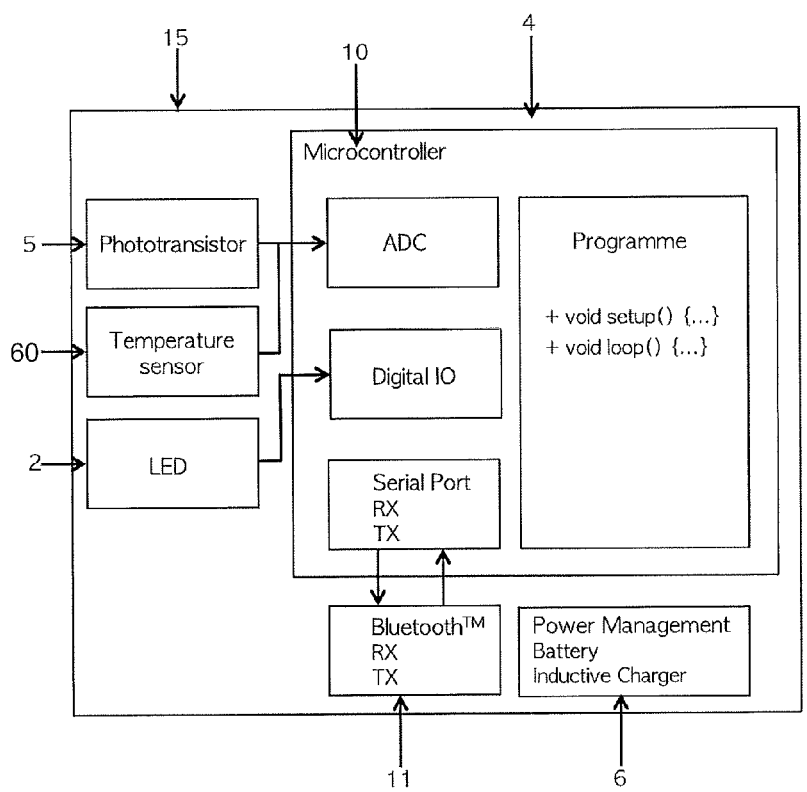

FIG. 6 shows a schematic of the components of FIG. 2 in further detail (FIG. 6A), and a schematic of the components of FIG. 2 with a temperature sensor 60 (FIG. 6B), and in particular shows the controller 10 and connected components. The controller is configured to connect with the wireless communications interface 11 to at least transmit and also receive data from an external system.

In some embodiments the wireless communications interface 11 is a radio transceiver. However, in other embodiments the interface 11 may be a transmitter only. The interface can be, for example, 2.4 GHz transceiver having a common communications protocol such as a Bluetooth transceiver. Other transmission frequencies and protocols may be used. In circumstances where long range communication is required, or communication through matter having substantial radio frequency attenuation, it can be beneficial to use lower frequencies such that wirelessly transmitted power can be kept relatively low to conserve battery power. However, higher transmission frequencies offer benefits such as smaller antennas and may therefore be most appropriately applied in circumstances where limited packaging space is available within the sensor housing 4. Further, in some embodiments the PCB track or flexible antennas are incorporated. Alternatively, the antenna extends externally to the sensor housing as long as appropriate shield materials suitable for sterilisation are used.

In various embodiments the controller 10 is configured to control energisation of the light source 2 and receive a signal from the receiver 5 indicative of the amount of light received. The controller can facilitate an automated process where, for example, the light source 2 is periodically energised and the receiver 5 output received and stored. Alternatively, the controller can respond to an instruction received via the communications interface 11 to make a measurement.

The controller 10 samples a voltage received from the light receiver 5 via an ADC input pin at periodic intervals. The signal the controller receives from the light receiver 5 is indicative of the light scattered or absorbed by solution within the optical path 3. The optical density of the solution can be determined from the received signal. As the solution becomes more optically dense, the intensity of the light received by the light receiver is reduced.

In some embodiments the controller has an ADC configured to sample the signal received from the light receiver. The sampled value can optionally be converted a measurement via Beer's Law or stored for later use and/or transmission to an external system. The controller can process the measurement internally, for example using preconfigured software, or the controller can output the raw value to the communications interface and an external processing system may then calculate the measurement value. The controller has a digital output configured to control energisation of output of the light source 2. The digital output may be configured to provide, for example, a PWM signal representing a desired intensity output. Such a PWM signal may be amplified by appropriate electronics should the controller output not be able to supply enough current on its own.

Figure 14:
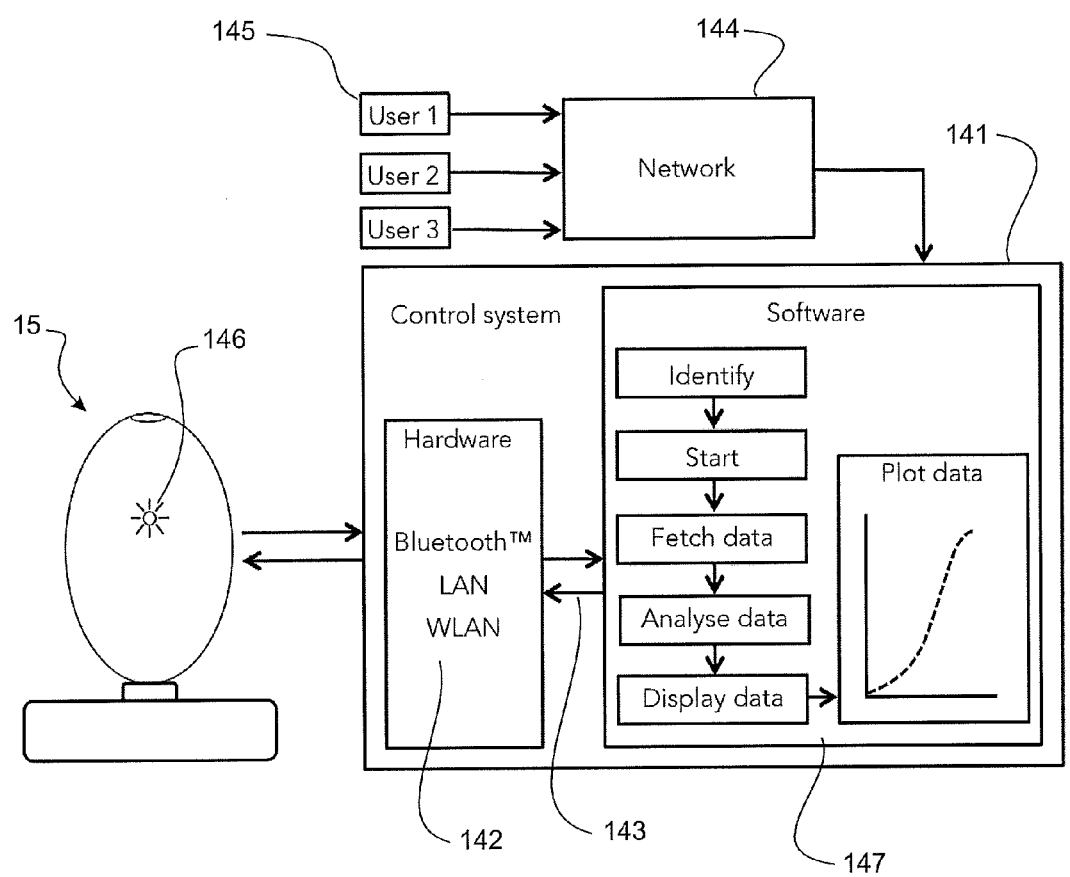
FIG. 14 shows a schematic of the components of the control system, network, and user interfaces.

FIG. 14 presents a schematic depicting one embodiment of the invention, in which one or more sensor devices 15 are controlled by a control system 141 (typically a PC or laptop) in the proximity of the one or more sensor devices. The control system is connected 143 to the one or more sensor devices, for example via Bluetooth 142, and to a computer network 144 for user interaction. Users 145 can remotely control or monitor the sensor devices by connecting to the control system. In one example, one or more of the sensor devices have an identifier 146, such as an LED, to differentiate the devices present. The identification process and other sensing aspects of the device can be triggered via software 147 running on the control system. In various embodiments the software is configured to identify one or more of the sensor devices, for example internally by a unique ID, to make it identify itself to the user (for example by LED), to control the measuring functions of the sensor device, to fetch recorded data from the sensor device, and/or to display and/or analyse the data.

To minimise power consumption, in some embodiments the controller is configured to pulse the light source or energise it only for short periods such as when the receiver output is being monitored. Energising the light source for at least 10 ms ensures that light source avoids detecting any transients and that the receiver output is likely to be stable. The light receiver receives enough light in order for it to make correct measurements and that intensity of the light source is constant.

The light receiver output is tuned such that it remains within a linear range and does not saturate. The linearity of response is ensured either by selection of the components during construction or dynamically by a configuration of programmable resistors that are connected to the controller to form voltage divider circuits and/or control the gain of an active signal amplifier. The programmable resistors can be set based on knowledge of the dynamic output range of the light receiver and/or light source to tune either the output sensitivity or intensity respectively. This allows the sensor to be configured to measure a wide range of optical densities and that configuration is changeable using the controller to implement changes in sensitivity and intensity.

In some embodiments, the sensor may incorporate a propulsion mechanism operable to provide motility of the sensor within a vessel. For example, in environments with large fluid volumes, the propulsion mechanism advantageously enables the sensor to operate to sample from several locations within the vessel, and wirelessly transmit the sample to a distal location. Propulsion can be achieved, for example, by having a rotatable fin mounted external to the sensor housing. Rotating the fin by way of a motor propels the sensor within the solution. The propulsion mechanism can also be used to replace a laboratory shaking or stirring platform by actively agitating the solution by the sensor moving in the solution and/or the sensor moving the solution relative to its position. This may be advantageous in circumstances where the optical density of a solution is desired to be known in a non-laboratory environment.

In some embodiments, the sensor incorporates a buoyancy control device. For example, buoyancy control may be desired in environments with vertically large fluid volumes such as beverage fermentation vats. The buoyancy control device advantageously enables the sensor to take measurements from many vertical locations as it rises and sinks. Alternatively, the buoyancy of the sensor could be selected to float or sink in a particular solution to be tested. Buoyancy control can be achieved, for example, by compressing a compressible fluid with a piston to change the internal density of the sensor. Alternatively, a fluid bladder can be used to draw solution into the bladder to change the buoyancy.

In certain embodiments, particularly where the sensor includes a buoyancy and/or a propulsion mechanism, the controller can be configured to actively control propulsion and/or buoyancy of the sensor in-situ. For example, the controller is configured to have the sensor move in the solution while recording measurements. For example, the sensor may be located in a vessel having a large vertical distance such as a fermenter. The sensor can travel the vertical distance by control of buoyancy and/or propulsion while also recording measurements to attain a continuous profile of the vessel. In other embodiments the buoyancy and/or a propulsion mechanism is operated in free form or a predetermined activation pattern. For example, when the buoyancy or propulsion mechanism is configured to cause the sensor to rise and/or sink one or more times.

In some embodiments the sensor includes a second light receiver and optical components configured to reflect a portion of the light transmitted by the light source to that second light receiver. The light received by the second light receiver is indicative of the output power from the light source and can be used as a calibration measure.

In some embodiments the sensor includes one or more temperature sensors arranged within the housing and configured to provide temperature information to the controller. For example, temperature sensors located proximate to the light receiver can be used to compensate for temperature related drift of the light receiver. A temperature sensor located near the power source can be used to indicate excessive temperature generation. A temperature sensor located in contact with or proximate a surface in contact with the environment, for example near the housing surface, or proximate the channel, can be used to indicate environment temperature information, for example solution temperature information.

The power source 6 is configured to provide power to the controller 10 and other components located within the housing 4. The most useful power source is a rechargeable battery. In this configuration, a charging system 7 is connected to the battery to provide a source of power from which the battery can be recharged. In this configuration the charging system has a wireless power transfer receiver. In other configurations, the charging system and battery may be replaced with a wireless power receiving device that continuously receives power to operate the sensor, or receives power at least when measurements are desired to be taken. Inductive power transfer technology may be used to apply power to the sensor or battery charging system from a remote location without the use of a wired connection.

The power system 7 incorporates appropriate electronics configured to convert a received wireless power signal into a voltage useful for charging the battery or powering electronics within the housing. The particular electronics and configuration required are dependent upon incoming wireless power transfer signals and the particular devices to be powered. Those skilled in the art will recognise the need for the electronic circuits to be tailored to the requirements. However, it is noted that rectification and/or DC to DC conversion circuits are most applicable. The controller 10 may further facilitate power management by, for example, monitoring the voltage of the battery 6 and communicating readings either facilitating transmission of a signal indicative of the need for recharging or automatically activate a recharging process.

In some embodiments the wireless charging system has a coil operating with a voltage of around 5V and frequency between 112-205 kHz on a 100 kHz tuned coil circuit with 5 W max power output. For optimum charging operation, the charging components can include Qi compliant inductive charging with device detection, power transmission management and foreign object detection.

To optimise sensor operation, the power management electronics and the communication electronics are physically separated by a practical distance to mitigate or eliminate electromagnetic or radio frequency interference creating undue noise. Further, separate ground planes between power management electronics and the communication electronics is beneficial to further isolate noise.

To provide power to the sensor a battery can be a single cell 3.7 V lithium ion polymer 110 mA/hr battery having 200 mA discharge and 100 mA charge rates. However any high energy density rechargeable battery could be employed. Alternatively, where the size of the sensor housing is not limited, lower density energy sources could also be used.

In some embodiments, one or more electromechanical kinetic energy harvesting mechanisms may be used in place of, or alongside, a wireless power transfer device to facilitate a source of power to recharge the battery 6. In this way, movement of the sensor while in use can generate electrical energy used to power onboard electronics or charge a battery. The time required to charge the battery in the sensor may be therefore reduced or not required.

The controller 10 may further be configured to use the light source 2 as a status indicator in configurations where the light source can be seen from outside the vessel containing the sensor. For example, the light source can be flashed to show a code indicative of parameters to a user in visual range. The code can be indicative of information such as, full memory or low battery, or for identification of a particular sensor in an environment where many sensing devices are simultaneously deployed.

Figure 4A:
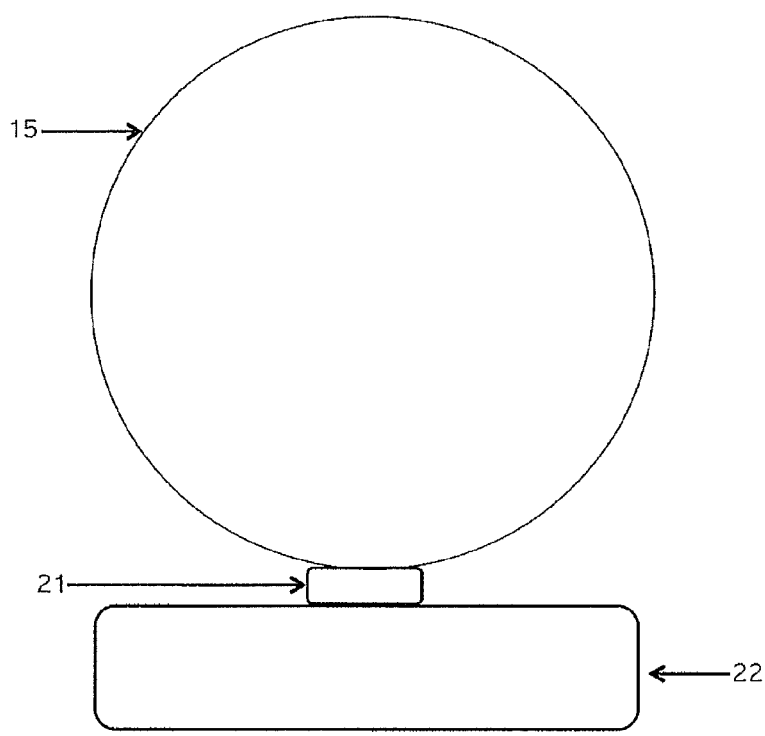
FIG. 4 shows a side elevation of a spherical (FIG. 4A) and a spheroid (FIG. 4B) sensor, and respective charging platforms.
Figure 4B:
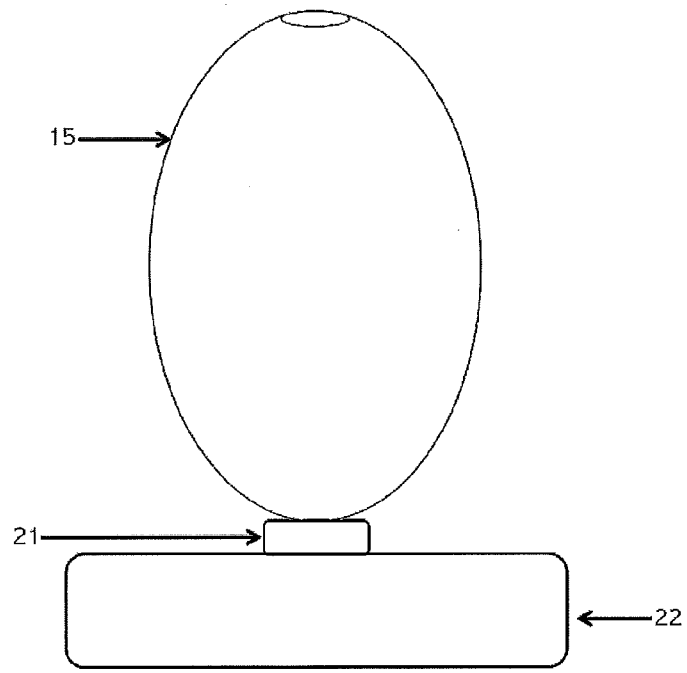
Figure 5A:
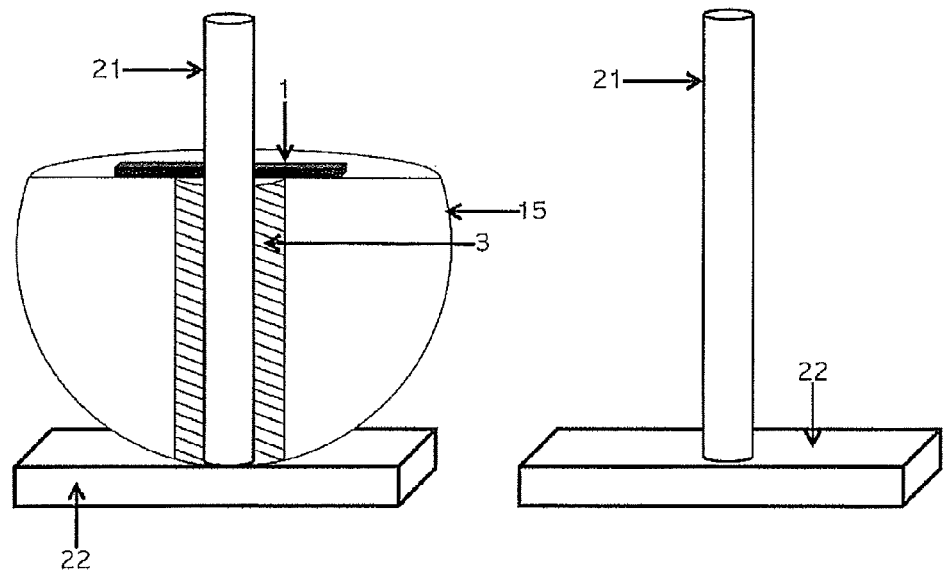
FIG. 5 shows a cross sectional view a spherical (FIG. 5A) and a spheroid (FIG. 5B) sensor and the charging platform of FIG. 4.
Figure 5B:
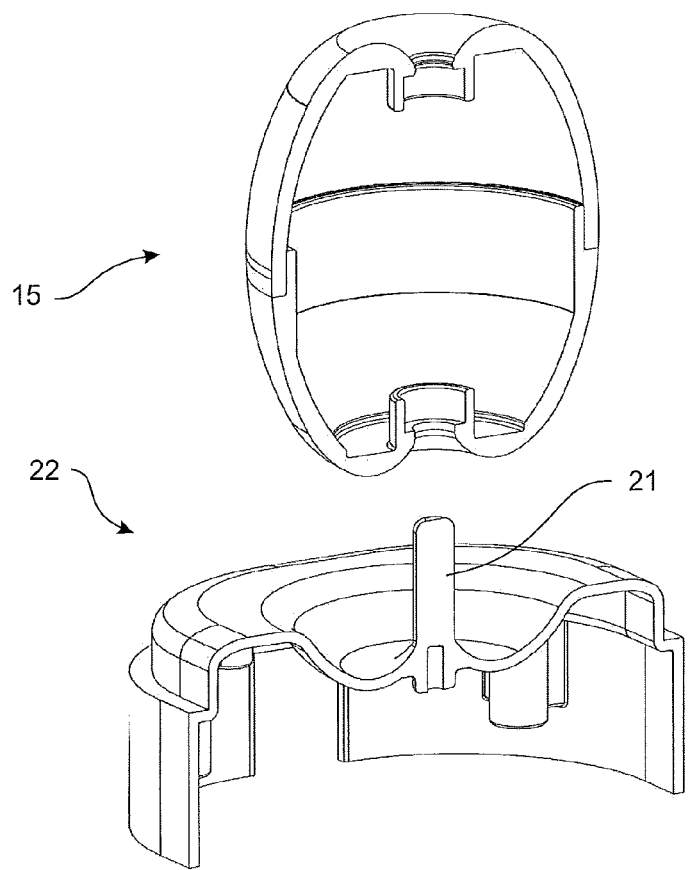

FIG. 4 shows a side elevation of a side elevation of a spherical (FIG. 4A) and a spheroid (FIG. 4B) sensor 15 residing on a spigot 21 that forms part of a charging platform 22. FIG. 5 shows a cross sectional view the sensor 15 and charging platform 22 of FIG. 4, and a perspective view of a charging platform 22 without a sensor attached. While the channel 3 of the sensor 15 performs the task of providing an opening that allows the solution to flow into the optical path between the light transmitter 5 and light receiver 4, it also provides a mounting receptacle that allows the sensor to be mounted securely to the platform. The spigot 21 of the platform 22 incorporates a wireless power transmission, or inductive charging device. The sensor 15 has the wireless power receiving device positioned proximate to the spigot 21 when mounted on the spigot to optimise wireless power transfer efficiency.

When the sensor 15 is not in use, it can be placed upon the platform 22 which then provides wireless power to charge the built in battery 6. The sensor 15 does not therefore require a wired interface for power transmission or recharging and the sensor has a charged battery when it is required to be used.

Figure 3:
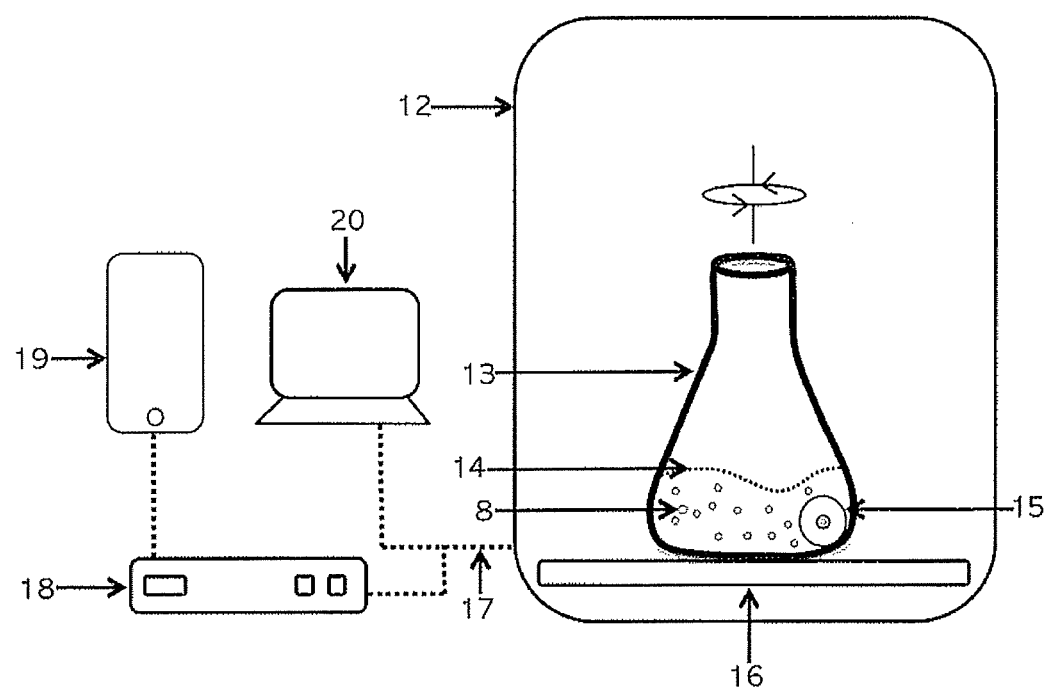
FIG. 3 shows an overview of the sensor in situ and proximate an external control system.

FIG. 3 shows an overview of the sensor 15 in-situ and proximate an external control system. The external control system is configured to work harmoniously with one or more sensors by being configured to respond to communication signals transmitted from one or more sensors, store data received from the one or more sensors and optionally display data.

The external control system comprises one or more computational devices and may comprise one or more of a stand-alone computer, laptop 20, smart phone 19 or tablet type device. A base station 18 may optionally be provided to interface one or more computational devices to one or more sensor devices 15. The base station 18 may comprise, for example, a wireless communications interface complementary to the wireless communications interface incorporated in the sensor.

The base station 18 may also comprise a wireless power transfer device adapted to provide a wireless power transfer signal to the sensor. The base station 18 may further comprise computational ability and provide a replacement for other computational devices. The base station 18 may further comprise one or more display devices adapted to display data such as a real time optical density measurement or sensor battery capacity status.

The sensor 15 is shown in use whereby it is immersed within a vessel 13 also containing a solution from which an optical parameter, such as the optical density, is desired to be measured. The vessel could be a beaker, flask or similar container. The vessel 13 is optionally located within an incubation cubicle 12 for control of the environmental temperature. The vessel optionally resides atop a plate that provides mechanical movement to the vessel to simulate stirring or agitation of the solution within.

Cell growth rate and/or density in a solution containing live cells can be determined by periodic measurement of optical density of the solution within the sensor channel 3. The sensor 15 determines a measure indicative of the optical density of the solution 8 and wirelessly transmits a signal indicative of the optical density to the base station 17 for further interpretation. The wirelessly transmitted data may optionally include identification information in the event several sensors are used in close proximity. In this way, the base station may determine the particular sensor from which a signal was received.

The base station may also be configured to transmit a signal to the sensor and the sensor configured to receive that signal and respond appropriately. For example, the base station may be configured to transmit a signal indicative of a sample value to be taken by the sensor. The sensor is configured to receive that signal, determine a measurement from the solution in the channel 3 and transmit data back to the base station 17. Alternatively, the sensor may transmit blocks of data at periodic intervals which allows the sensor to sample over a longer time period than continuously transmitting data. This minimises the energy consumption associated with data transmission, or for extending operation time should the battery energy be depleted. The base station may further be configured to control activation of any propulsion or buoyancy control within the sensor.

FIG. 12 shows a spherical embodiment (FIG. 12A-12C) and a spheroid embodiment (FIG. 12D-12F) of the sensor 15 optimised for use in a laboratory vessel and with an optimised layout of the internal components. In particular, FIG. 12A shows a front view and cross sectional view AA, FIG. 12B shows a side view and cross sectional view BB, and FIG. 12C shows a top view and cross sectional view CC.

The sensor 15 has two joinable hemispherical shell sections, an upper shell section 31 and a lower shell section 32. The shell sections can be joined by a releasable mechanism such as an interference fit or threaded connection.

The channel 3 is formed from a borosilicate (for example, Pyrex™) tube that extends from one extent of the shell to the other. The channel 3 is sealed to the shell sections by o-rings 30. A light source 2 and light receiver 5 are disposed about the channel.

A collimator 23 is provided proximate the light source and receiver to guide light through the channel, minimise light scattering and minimise ambient light from entering the light receiver.

A battery 6 is located in one portion of the housing and one that is distant from the location of the wireless communication device 11 to minimise shadowing of radio signals. The wireless communication device 11 is a Bluetooth transceiver module. A controller 10 is connected to the wireless communication device 11, the light source 2 and the light receiver 5.

Figure 12A:
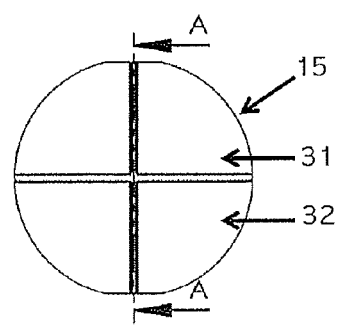
FIG. 12 shows a spherical (FIG. 12A-12C) and a spheroid (FIG. 12D-12F) sensor and a layout of the components within the sensor.
Figure 12A:
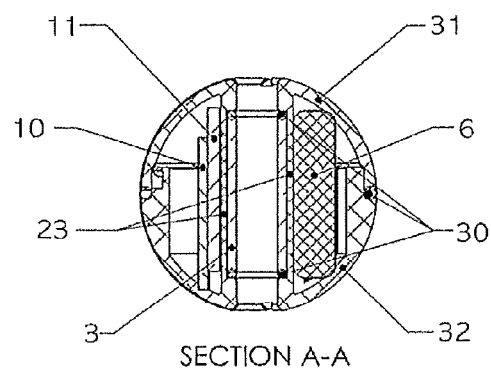
Figure 12B:
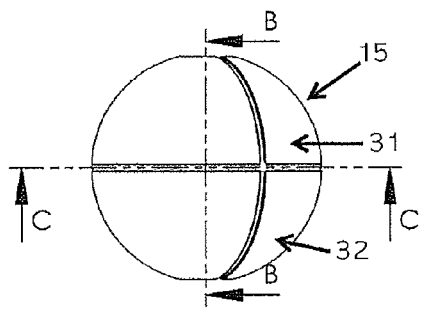
Figure 12B:
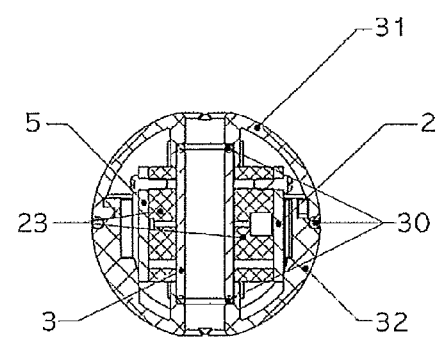
Figure 12C:
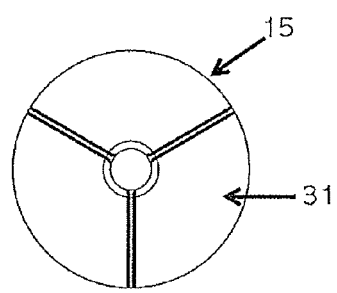
Figure 12C:
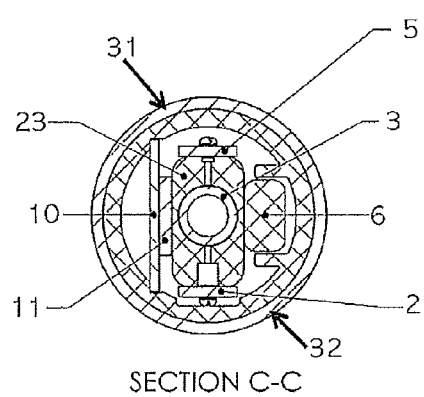
Figure 12D:
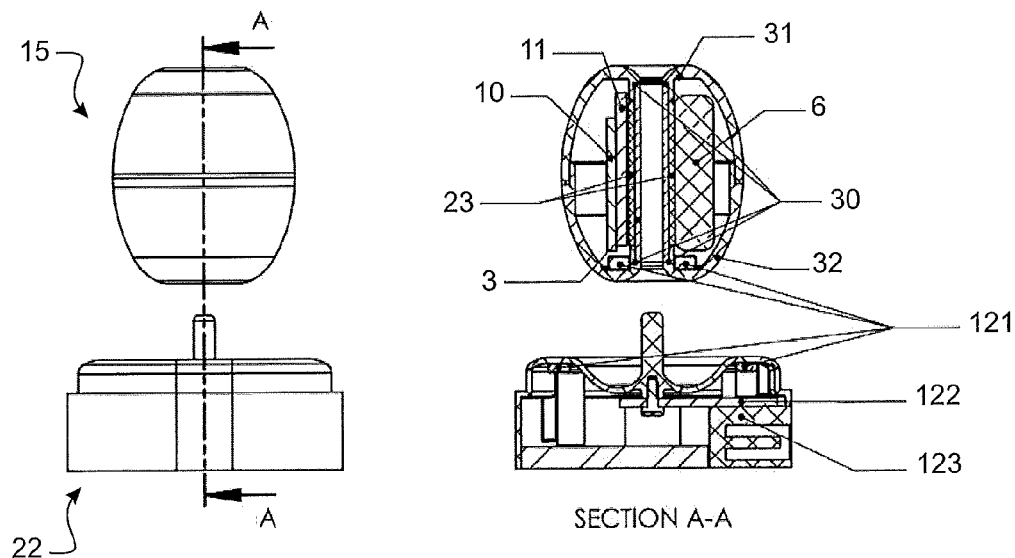
Figure 12E:
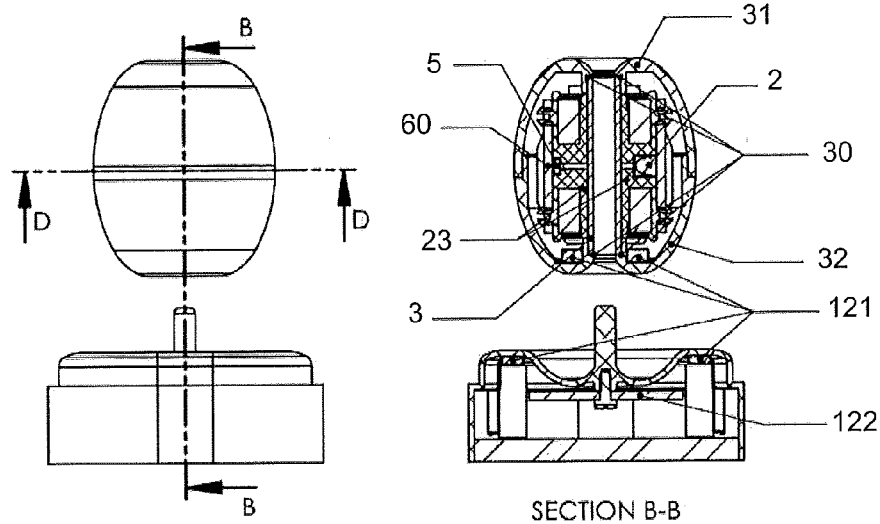
Figure 12F:
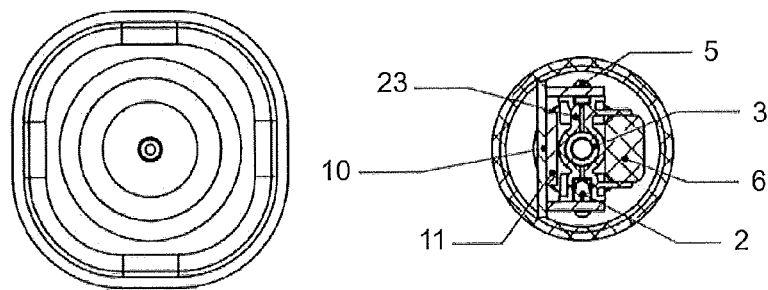

FIG. 12D shows a front view and cross sectional view AA, FIG. 12B shows a side view and cross sectional view BB, and FIG. 12C shows a top view and cross sectional view CC, of the spheroid sensor 15.

The sensor 15 has two joinable hemispherical shell sections, an upper shell section 31 and a lower shell section 32. The shell sections can be joined by a releasable mechanism such as an interference fit or threaded connection.

The channel 3 is formed from a borosilicate (for example, Pyrex™) tube that extends from one extent of the shell to the other. The channel 3 is sealed to the shell sections by o-rings 30. A light source 2 and light receiver 5 are disposed about the channel.

A collimator 23 is provided proximate the light source and receiver to guide light through the channel, minimise light scattering and minimise ambient light from entering the light receiver.

A battery 6 is located in one portion of the housing and one that is distant from the location of the wireless communication device 11 to minimise shadowing of radio signals. The battery is connected to a charging coil or coils 121 in the sensor 15, in which current is induced when the sensor 15 is placed on the charging platform 22 by a charging coil or coils 121, optionally forming part of a charging PCB 122, present in the charging platform 22 and the charging platform is powered, for example via a DC jack 123. The wireless communication device 11 is a Bluetooth transceiver module. A controller 10 is connected to the wireless communication device 11, the light source 2 and the light receiver 5.

FIG. 13 shows the representative spherical (FIG. 13A-13C) and the spheroid (FIG. 13D-13F) sensors of FIG. 12 with dimensions provided. In particular, FIG. 13A shows a cross sectional view AA as depicted in FIG. 13B, FIG. 13C shows a cross sectional view BB as depicted in FIG. 13B, FIG. 13D shows a cross sectional view GG as depicted in FIG. 13E, and FIG. 13F shows a cross sectional view EE as depicted in FIG. 13E.

Figure 13A:
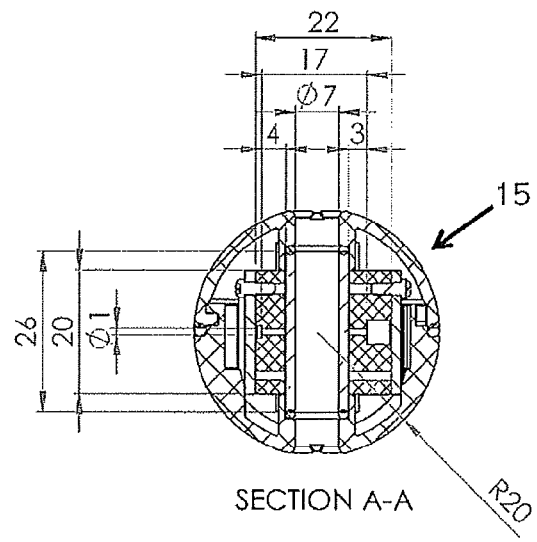
FIG. 13 shows the representative spherical (FIG. 13A-13C) and the spheroid (FIG. 13D-13F) sensors of FIG. 12 with dimensions provided.
Figure 13B:
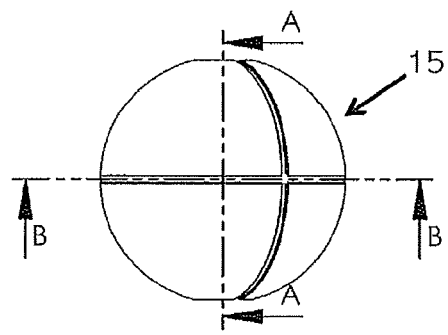
Figure 13C:
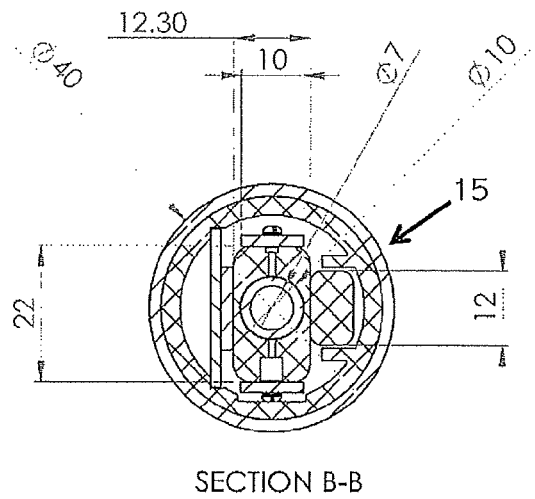
Figure 13D:
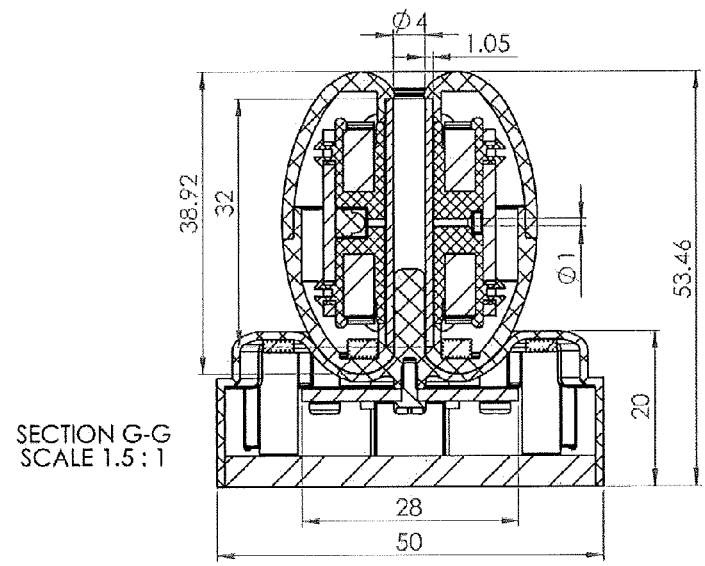
Figure 13E:
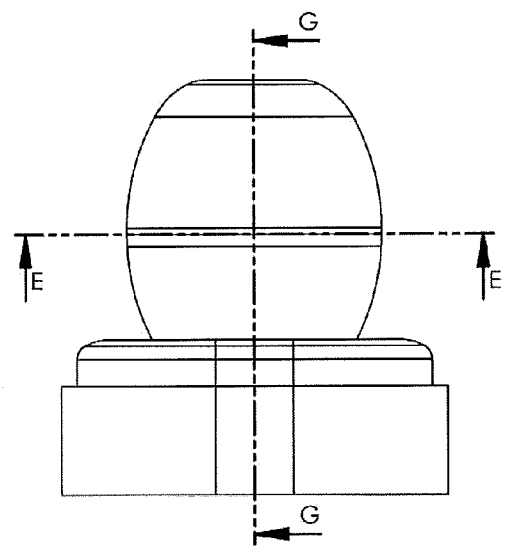
Figure 13F:
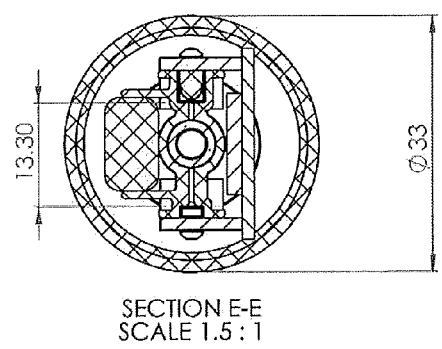

Key dimensions in the representative spherical sensor of FIG. 13A-13C include the outer sensor dimension of 40 mm and the channel 3 inner dimension of 7 mm. The width of the beam of light is 1 mm and the distance between the light source and detector is 22 mm. Key dimensions in the representative spheroid sensor of FIG. 13D-13CF include the outer sensor diameter of 33 mm and length of 39 mm, and the channel 3 inner dimension of 4 mm. The width of the beam of light is 1 mm and the distance between the light source and detector is 13 mm.

Use of the sensor 15 may further include one or more of the following steps, in any order:

The sensor is placed on the charging base such that the spigot 21 is inserted within the channel 3 that extends through or partly through the sensor housing.

The sensor is charged using the wirelessly coupled base station 22 or similarly capable device.

The transmitter in the sensor is connected with a receiver to facilitate wireless communication therebetween.

The sensor is placed inside a vessel containing a solution to be measured.

The vessel containing the sensor is placed upon a mechanical stirring or shaking device such as a shaker incubator to agitate the solution in the vessel.

The base station transmits a signal to the sensor when a measurement is desired.

The controller receives a signal that a measurement is desired, causes energisation of the light source, measures the signal from the light receiver and outputs information to be transmitted to the base station.

The controller is configured to cause energisation of the light source, measure the signal from the light receiver and output information to be transmitted to the base station.

The controller is configured to cause energisation of the light source, measure the signal from the light receiver and store measured signals to later be transmitted to the base station.

The controller measures the remaining battery capacity. If the capacity is determined to be low, an additional energy harvesting mechanism such as an electro-mechanical generator may operate to convert kinetic energy of the sensor into electricity to charge or supplement the battery.

Cleaning the sensor using, for example, a 70% ethanol solution, for re-use.

The sensor may operate to achieve a measurement by using one or more of the following steps, in any order:

Energise the light source 2 for a predetermined period of time. For example, the light source is energised for approximately ten milliseconds.

Measure one or more samples indicative of the light received by the light receiver 5. For example, approximately five samples are recorded by the controller.

Perform a statistical calculation of the measured samples. The most useful statistical calculation is where the average of several samples is calculated. Those skilled in the art will appreciate that other statistical or filtering calculations could be performed, or several performed and combined where circumstances dictate that this would provide a more meaningful measure.

The sensor has numerous advantages, including:

A housing that entirely seals internal components from the environment whilst being able to be submerged within a solution to be tested.

The sensor can be constructed from a material that is easily chemically sterilised for repeated use in a variety of applications.

The sensor is sealed and self contained which helps to prevent contamination.

The sensor is stored and used remotely from the base station without requiring a wired interface.

The sensor can be transported with a vessel containing a solution, for example, between a storage area and a shaking table where a solution is to develop.

The sensor is able to be mobile while immersed in a solution thereby improving the ability of the sensor to provide measurements from a variety of locations within the vessel.

EXAMPLE 1

Assaying Optical Density of Microorganism Culture

Preliminary testing of a sensor 15 was conducted alongside measurements gathered using an Eppendorf BioPhotometer Plus bench top spectrophotometer simulating a typical yeast growth assay.

A widely used laboratory strain *Saccharomyces cerevisiae:* W303 was cultured overnight to exponential phase in YPD complete media and the cells were collected by centrifuge.

The sensor 15 was sterilized in 70% ethanol and added to fresh media in a sterile culture flask before being placed inside an incubator containing an orbital shaker.

A baseline measurement was taken following a period of approximately ten minutes to allow for temperature equilibration. The base line data output was stable regardless of shaker motion, internal lighting, or shielding of external ambient light. Cells were added to the media at an initial inoculation to $OD_{600nm}$ 0.1 as measured by the Eppendorf spectrophotometer.

Cells were then added to the culture media at a volume equivalent to 0.1 $OD_{600nm}$ units and at each point measurements were made in parallel using both the commercial spectrophotometer and sensor 15 up to a final density of 0.8 $OD_{600nm}$.

As measurements using the commercial spectrophotometer involved removal of a small sample from the culture, dilution and pipetting into a cuvette, there is some error resulting from the numerous small volume liquid handling steps which is apparent in the data supplied and typical for this type of measurement.

Figure 7:
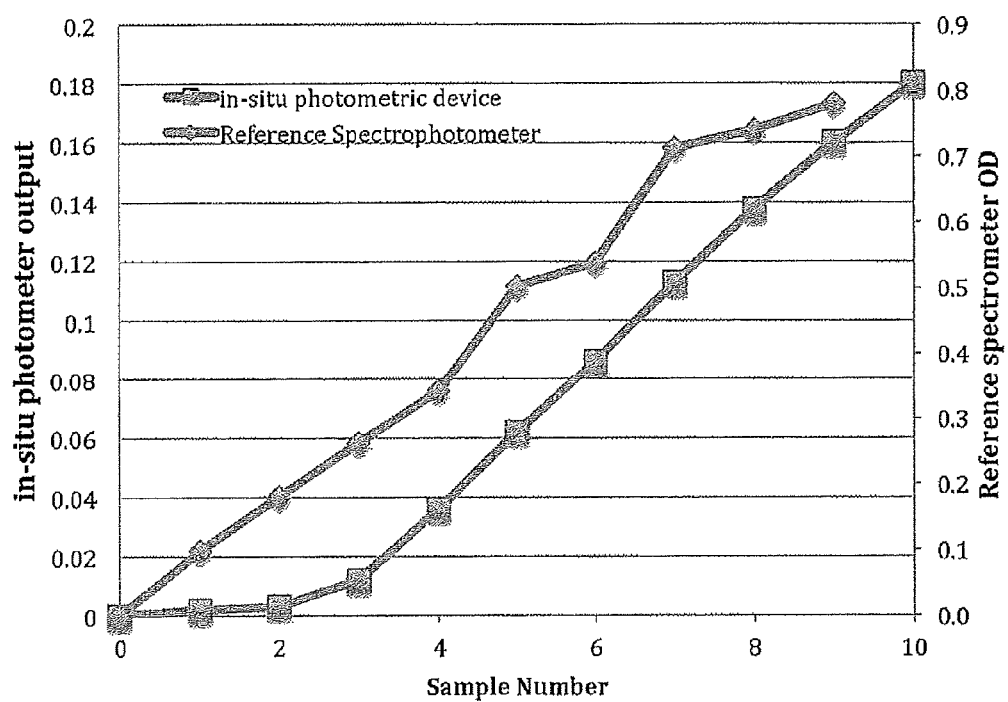
FIG. 7 shows a graph comparing the results obtained with a sensor and a bench top spectrophotometer as described in Example 1.

FIG. 7 shows a comparison of the sensor 15 and the bench top spectrophotometer. In-situ photometric device measurements were obtained by averaging 14 samples each consisting of an averaged value of 5 intensity measurements. Manual triggering (in rapid succession) of the measurements were used to obtain the intensity data after addition of each aliquot of cells.

As can be seen, the data provided by the in-situ device of the present invention provides a response to the change in optical density during the course of the experiment. In the case of non-linear response due to saturation, the non-linearity can be corrected by precalibration of the device over the expected optical density range, before deployment. In the case of remaining in the linear regime, no such calibration is required and the results may be directly interpreted and in this case accuracy at least comparable to standard measurement equipment is obtained.

In this specification, where reference has been made to external sources of information, including patent specifications and other documents, this is generally for the purpose of providing a context for discussing the features of the present invention. Unless stated otherwise, reference to such sources of information is not to be construed, in any jurisdiction, as an admission that such sources of information are prior art or form part of the common general knowledge in the art.

Where in the foregoing description reference has been made to elements or integers having known equivalents, then such equivalents are included as if they were individually set forth.

Although the invention has been described by way of example and with reference to particular embodiments, it is to be understood that modifications and/or improvements may be made without departing from the scope or spirit of the invention.

INDUSTRIAL APPLICABILITY

The devices and systems of the invention, and the methods of using them have application in a wide range of industries and environments, including medical, biotechnological and pharmaceutical research and production, food and beverage technologies, industrial processing, the horticultural and agricultural sectors, and others.

We claim:

1. A measurement device adapted for in situ light intensity sensing from within an environment comprising:
   a housing adapted to enclose a control system and fluidly seal the control system from the environment, the housing having an outer wall and a channel fluidly connected to the environment at one or more locations,
   the control system comprising a controller, a light receiver component and a wireless data transmitter component,
   the light receiver disposed within the housing to receive light from the channel and output one or more signals indicative of light intensity, and
   wherein the control system is configured to:
   receive the one or more signals indicative of light intensity from the light receiver, and
   output a signal indicative of light intensity to the wireless data transmitter, and
   wherein the housing comprises a first and a second shell section, the first shell section having an engageable sealing surface adapted to couple with an engageable sealing surface of the second shell section, and form, when engaged, a substantially hermetic shell that encloses the control system, wherein the sealing surfaces of the first and second shell sections are threaded, are adapted to engage by interference fit, are adapted to compress about an o-ring, are chemically or thermally bonded, or any combination thereof.

2. The measurement device as claimed in claim 1 wherein the control system further comprises a light source disposed within the housing to define a light path that extends from the light source, through the channel to the light receiver.

3. The measurement device as claimed in claim 1 wherein a plurality of optical elements are disposed within the light path and are arranged to prevent light travelling substantially non parallel to the optical path or wherein a plurality of optical elements are disposed within the channel and are arranged to prevent light incident to the channel.

4. The measurement device as claimed in claim 1 wherein the channel extends between at least two locations on the outer wall of the housing to define a fluid flow path between the at least two locations.

5. The measurement device as claimed in claim 1 wherein the channel meets the outer wall of the housing at an acute angle in at least one location.

6. The measurement device as claimed in claim 1 wherein the channel is adapted to receive a spigot containing wireless power transfer electronics or one or more wireless power transfer components.

7. The measurement device as claimed in claim 1 wherein the outer wall of the housing is substantially spherical or at least has a substantially circular profile.

8. The measurement device as claimed in claim 1 wherein the control system further comprises one or more of the following:
   a temperature sensor,
   a propulsion mechanism operable to propel the device when in-situ, the controller further configured to output a signal to cause operation of the propulsion mechanism, and
   a buoyancy mechanism operable to cause floating or sinking of the device when in-situ, the controller further configured to output a signal to cause operation of the buoyancy mechanism.

9. The measurement device as claimed in claim 1 wherein the control system further comprises a wireless power receiver, the receiver disposed within the housing proximate the channel so as to receive wireless power signals emitted from within the channel or the receiver proximate the exterior surface so as to receive wireless power signals emitted proximate the exterior surface.

10. The measurement device as claimed in claim 1 wherein the control system further comprises a plurality of gain setting resistors and the controller is configured to change the configuration of the resistors to affect one or more of the dynamic voltage range output from the light receiver and/or the intensity of the light source.

11. The measurement device as claimed in claim 9 wherein the wireless power receiver is configured to provide a source of received charging power to a power source.

12. The measurement device as claimed in claim 1 wherein the housing further comprises a first aperture fluidly connected to the environment.

13. The measurement device as claimed in claim 1 wherein a tube is disposed within the first aperture and the inside of the tube is arranged to fluidly connect with the environment and the outside of the tube is adapted to seal the housing from the environment.

14. The measurement device as claimed in claim 1 wherein the housing further comprises two apertures and the tube is adapted to extend from the first aperture to the second aperture to define a fluid path through the housing.

15. The measurement device as claimed in claim 13 wherein the tube is disposed within the light path.

16. The measurement device as claimed in claim 13 wherein the tube is an optically transparent material.

17. The measurement device as claimed in claim 1, further comprising a data processing device,
   wherein the data processing device comprises a wireless data receiver configured to receive data transmitted by the wireless data transmitter.

18. The measurement device according to claim 17, the sensor device comprising a wireless data transmitter configured to wirelessly transmit a signal indicative of an optical density measurement to the data processing device, and
   the data processing device comprising a receiver adapted to receive a signal indicative of optical density measurements.

19. The measurement device as claimed in claims 17 wherein the device is configured to perform one or more of the following steps:
   store data received by wireless data receiver on a storage device,
   compute one or more statistical calculations on the stored data, and
   determine a measure of the optical intensity within the channel,
   output a value indicative of the measure of the optical intensity within the channel to a display,
   store data indicative of the time data is received from by the wireless data receiver, transmit the stored data to one or more portable computation devices, or display received data.

* * * * *